(12) United States Patent
Soyama et al.

(10) Patent No.: US 8,138,256 B2
(45) Date of Patent: Mar. 20, 2012

(54) FLAME-RETARDANT RESIN COMPOSITION

(75) Inventors: Makoto Soyama, Minato-ku (JP);
Kazuhiko Inoue, Minato-ku (JP);
Masatoshi Iji, Minato-ku (JP)

(73) Assignee: NEC Corporation, Tokyo (JP)

( * ) Notice: Subject to any disclaimer, the term of this patent is extended or adjusted under 35 U.S.C. 154(b) by 474 days.

(21) Appl. No.: 10/590,237

(22) PCT Filed: Feb. 23, 2005

(86) PCT No.: PCT/JP2005/002904
§ 371 (c)(1),
(2), (4) Date: Aug. 22, 2006

(87) PCT Pub. No.: WO2005/083004
PCT Pub. Date: Sep. 9, 2005

(65) Prior Publication Data
US 2008/0269361 A1    Oct. 30, 2008

(30) Foreign Application Priority Data

Feb. 27, 2004 (JP) ................................. 2004-054142
Oct. 13, 2004 (JP) ................................. 2004-298861

(51) Int. Cl.
*C08K 3/34* (2006.01)
(52) U.S. Cl. ......... 524/444; 523/218; 524/423; 524/430
(58) Field of Classification Search ................... 524/439
See application file for complete search history.

(56) References Cited

U.S. PATENT DOCUMENTS

| | | | |
|---|---|---|---|
| 3,331,671 A * | 7/1967 | Goodwin | 65/526 |
| 4,243,575 A | 1/1981 | Myers et al. | |
| 4,560,712 A * | 12/1985 | Chiang | 523/220 |
| 5,047,145 A | 9/1991 | Hwang | 209/166 |
| 5,505,766 A * | 4/1996 | Chang | 95/134 |
| 5,837,757 A * | 11/1998 | Nodera et al. | 524/87 |
| 6,379,797 B1 | 4/2002 | Nikkeshi et al. | |

FOREIGN PATENT DOCUMENTS

| | | |
|---|---|---|
| DE | 3027850 A1 | 2/1981 |
| EP | 1-026131 A | 8/2000 |
| JP | 8-104775 A | 4/1996 |
| JP | 2000-230123 A | 8/2000 |
| JP | 2000-336254 A | 12/2000 |
| JP | 2001-072853 A | 3/2001 |
| JP | 2001-152030 A | 6/2001 |
| JP | 2001-220193 A * | 8/2001 |
| JP | 2003-518539 A | 6/2003 |
| JP | 2003-518543 A | 6/2003 |
| JP | 2004-10825 A | 1/2004 |
| JP | 2004-43641 A | 2/2004 |
| WO | 9937592 A1 | 7/1999 |
| WO | WO 99/37592 * | 7/1999 |

OTHER PUBLICATIONS

Kulkarni et al, Studies on Fly Ash-Filled Epoxy-Cast Slabs Under Compression, Journal of Applied Polymer Science, vol. 84, 2404-2410 (2002).*
Gilman J.W. et al., "Flame Retardant Mechanism of Silica", 9th Int. Conf. Addit., 2000; (55-78).
Kashiwagi Takashi, et al., "Flame-Retardant Mechanism of Silica: Effects of Resin Molecular Weight", J. Appln. Polym. Sci., 87; 1541-1553 (2003).
Chand Navin, et al., "Development, structure and strength properties of PP/PMMA/FA blends", Bull Mater Sci., 23; 103-107 (2000).
Nikkeshi Susumu et al., The Effects of Addition of Surface-treated Silica Particle in Polycarbonate Composites, J. Jpn. Soc. Polym. Progress, (Seikei Kakou), vol. 10; No. 11, 891-897 (1998).
Kashiwagi Takashi, et al., "Flame Retardant Mechanism of Silica Gel/Silica", Fire Mater., 24; 277-289(2000).
Levchik Cf. et al., "Mechanisms of action in flame retardant reinforced nylon 6", Polymer Degradation Stability, 54; 361-363 (1996).
Kondoh Motohiro, et al. "Effective Utilization of Ash from Fluidized-Bed by Adding it to Polypropylene Resin", J. Chem. Eng. Jpn. (Kagakukogyo Rombun Shu), 25; 374-379 (1999).
Iji Masatoshi et al., "Silicone Derivatives as New Flame Retardants for Aromatic Thermoplastics Used in Electronic Devices", Polymers for Advanced Technologies, 9, 593-600 (1998).

* cited by examiner

*Primary Examiner* — Doris Lee
(74) *Attorney, Agent, or Firm* — Sughrue Mion, PLLC

(57) ABSTRACT

Disclosed is a flame-retardant resin composition which comprises inorganic particles, preferably a fly ash, containing a complex of silicon dioxide and aluminum oxide and having D50 of 1 to 10 μm.

10 Claims, 5 Drawing Sheets

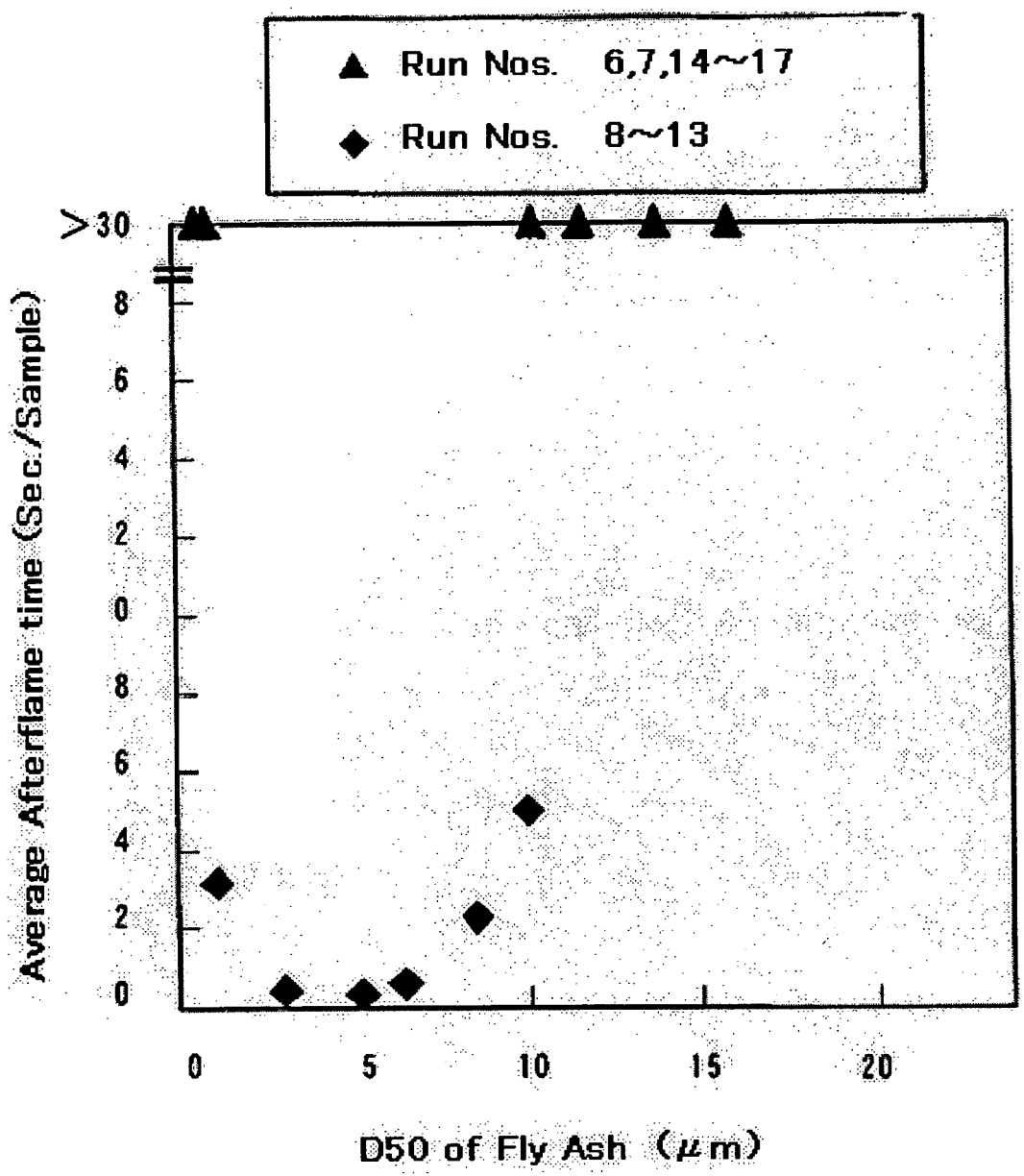

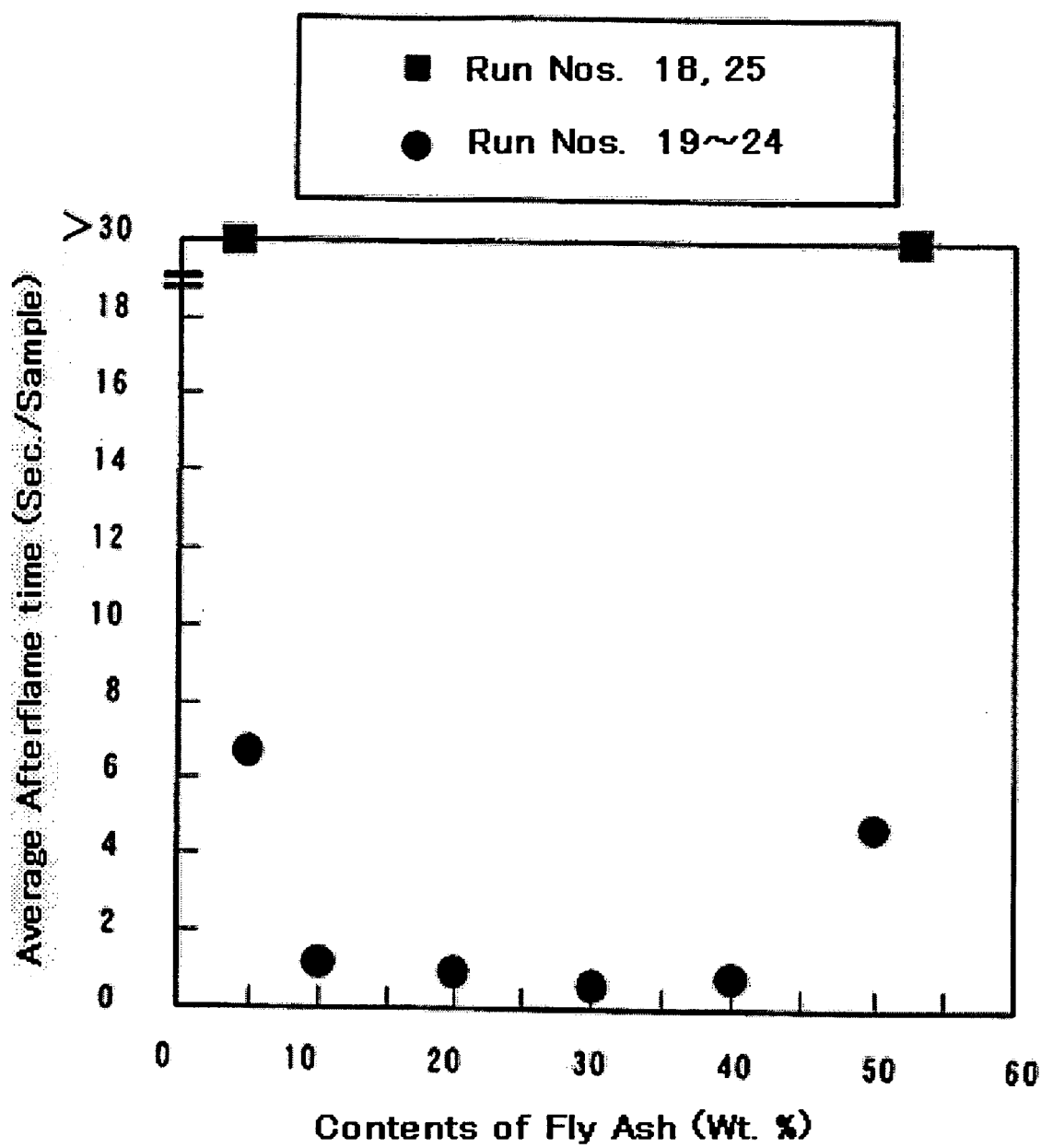

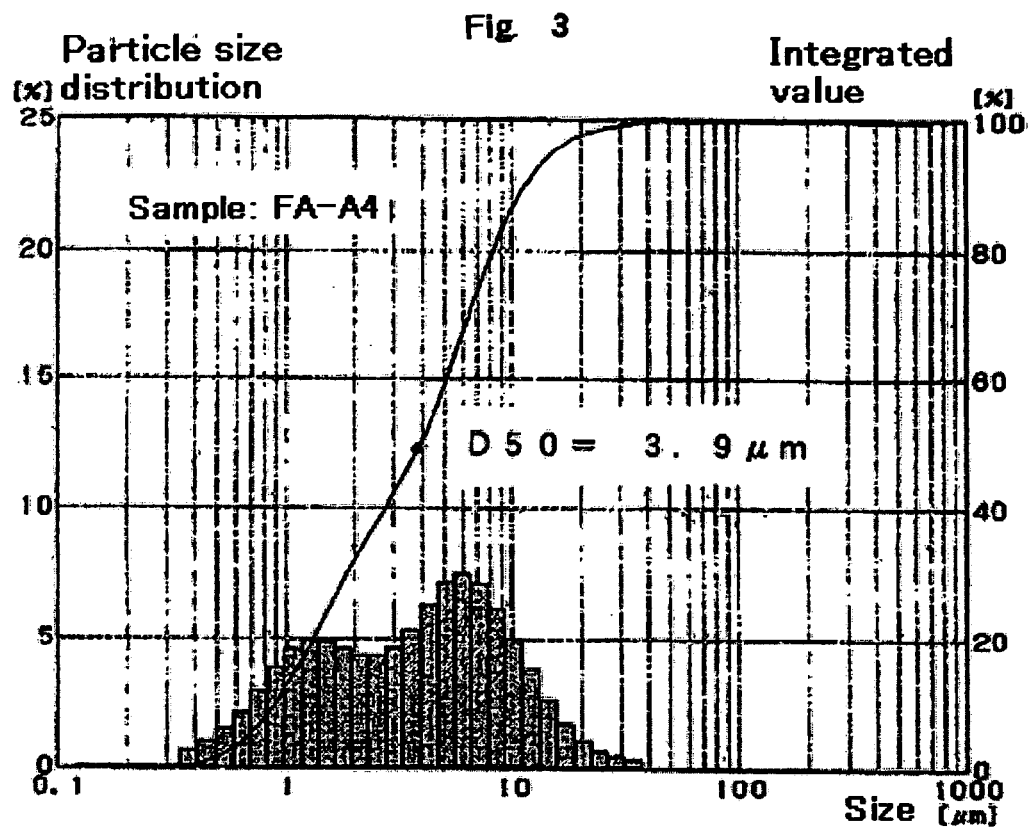
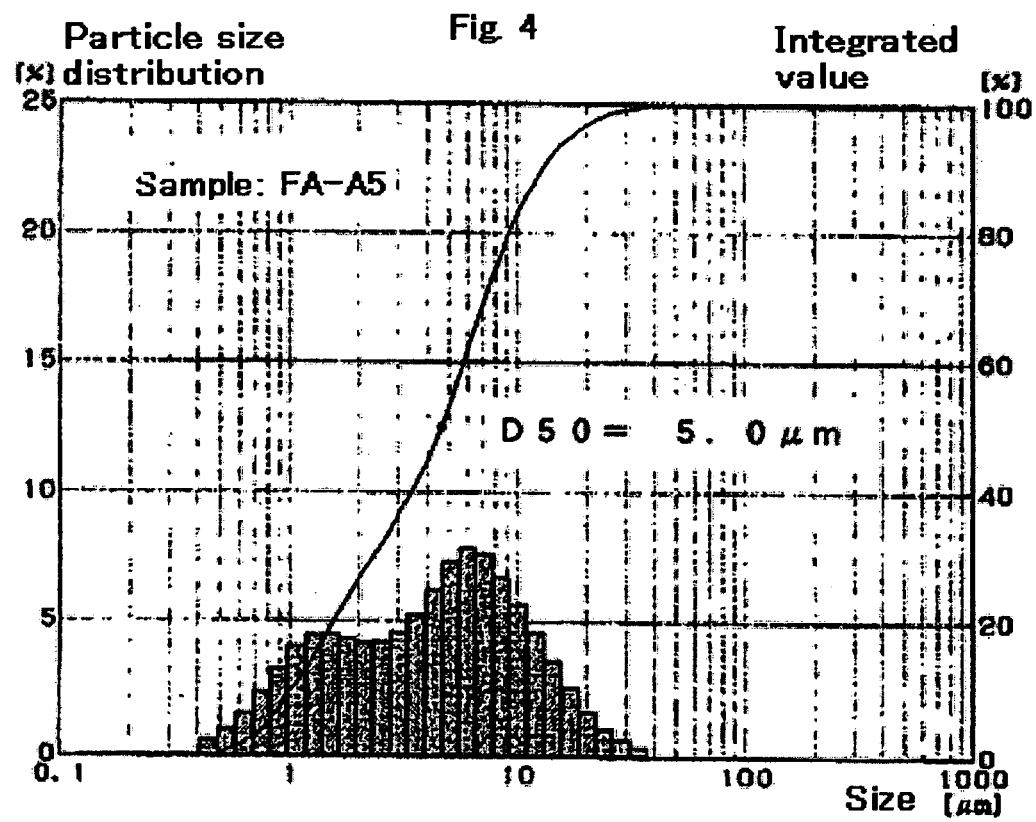

FLAME-RETARDANT RESIN COMPOSITION

This application claims priority from PCT Application No. PCT/JP2005/002904 filed Feb. 23, 2005, and from Japanese Patent Application Nos. 2004-054142 and 2004-298861, filed Feb. 27, 2004 and Oct. 13, 2004, respectively, which applications are incorporated herein by reference.

TECHNICAL FIELD

The present invention relates to a flame-retardant resin composition as well as to a flame-retardant molding material or molded article using the composition.

BACKGROUND ART

Resin compositions used in the filed of electric and electronic appliances are required to have superior flame retardancy for their safety; therefore, extensive research and development has been made for "flame-retardant resins". Polycarbonate type resins have excellent heat resistance, excellent electrical properties, etc. and accordingly they are being actively developed as a resin material for flame-retardant resin composition.

Currently, resin compositions used in the filed of electric and electronic appliances are required to have even higher flame retardancy and it is being attempted to further improve the flame retardancy of polycarbonate type resins by adding thereto various flame retardants.

Brominated compounds, phosphorus compounds, etc. have been used as conventional flame retardants. In recent years, however, it has been required to achieve flame retardancy without using any halogen atom. In such a situation, it is being attempted to improve the flame retardancy of polycarbonate type resins by compounding thereinto a small amount of inorganic particles.

In, for example, JP-A-2004-010825 (Patent Literature 1) is disclosed a flame-retardant resin composition wherein inorganic particles of silica or the like are compounded into an aromatic polycarbonate. Specifically explaining, consideration is made on the shape of the inorganic particles compounded, in order to improve the flame retardancy of aromatic polycarbonate.

Also, JP-A-2001-152030 (Patent Literature 2) discloses a flame-retardant material which contains particles of 10 to 100 nm in particle size obtained by grinding an inorganic porous material loaded with a flame retardant. Exactly, it is a flame-retardant resin material obtained by firing an inorganic material such as porous glass, silicon oxide, aluminum oxide or the like to form a porous material, loading thereon an additive (a flame retardant) selected from metals, metal salts and inorganic compounds, then passing the additive-loaded porous material (particles) and a resin (e.g. a polycarbonate or a polypropylene) through a twin-screw extruder to conduct fine pulverization and mixing simultaneously. It is described in the Patent Literature 2 that, in the flame-retardant material, the additive is dispersed well and thereby flame retardancy is achieved.

Patent Literature 1: JP-A-2004-010825
Patent Literature 2: JP-A-2001-152030

DISCLOSURE OF THE INVENTION

Problems to Be Solved by the Invention

With the above-mentioned conventional techniques, however, it has been difficult to realize a high level of flame retardancy stably. That is, the flame retardancy achieved by compounding inorganic particles into a polycarbonate type resin tends to be superior to the flame retardancy of conventional polycarbonate type resins; however, the flame retardancy has not passed the V-0 standard specified in the UL 94 test (a combustibility test for a plastic material for appliance part), known as a standard for high flame retardancy and further has been unable to pass the V-2 standard also specified in the above test.

Also in resins other than polycarbonate type resins, various investigations have been made on materials for enhancing flame retardancy. However, in any combination studied, it has been difficult to realize sufficient flame retardancy stably.

The present invention has been made in view of the above problems and aims at obtaining a polycarbonate resin composition of superior flame retardancy stably.

Means for Solving the Problems

According to the present invention, there is provided a flame-retardant resin composition containing a polycarbonate type resin and inorganic particles, wherein the inorganic particles contain particles composed of a complex of silicon dioxide and aluminum oxide and have a 50% particle size (D50) of 1 to 10 μm. The present invention is the above flame-retardant resin composition in which the inorganic particles are contained in the total composition in an amount of 1 to 60 weight %.

Also, according to the present invention, there is provided the above flame-retardant resin composition in which the inorganic particles are fly ash.

The flame-retardant resin composition of the present invention contains a polycarbonate type resin and inorganic particles, wherein (i) the inorganic particles contain at least a complex of silicon dioxide and aluminum oxide and (ii) the particle sizes of the inorganic particles are controlled in a particular range. As described in the portion of Background Art, there are some examples that the techniques of compounding silica particles or alumina particles into a resin was studied, and however, there is no study that particles containing a complex of silicon dioxide and aluminum oxide are used therefor. In the present invention, by using inorganic particles containing such a complex, there has been realized superior flame retardancy which is unobtainable with silicon dioxide particles alone, aluminum oxide particles alone, or a mere mixture thereof.

The reason why improved flame retardancy is obtained by the above constitution is not clear. However, the reason is considered to be that, when the present resin composition has caught fire, the above-mentioned particular inorganic particles act on the polycarbonate type resin to form a structure which is resistant to combustion.

Preferably, the inorganic particles of the present invention contain aluminum oxide particles and silicon dioxide particles, in addition to the particles containing the above-mentioned complex. The aluminum oxide particles and silicon dioxide particles used here are, respectively, particles containing aluminum oxide as a main component and particles containing silicon dioxide as a main component, and may contain other components in a very small amount. The present resin composition has improved flame retardancy by using inorganic particles consisting of particles of a complex of silicon dioxide and aluminum oxide, silicon dioxide particles and aluminum oxide particles. This reason is not clear, but is presumed to be that the action of inorganic particles on polycarbonate type resin is exhibited more reliably.

A preferred example of the inorganic particles is fly ash. Fly ash is a generic term used to refer to the combustion ash generated in thermal power plant and refers to, in particular, a finely pulverized coal ash generated at, for example, a thermal power plant wherein coal is burnt by a pulverized coal combustion method. In JP-A-2000-336254, for example, is disclosed a technique of adding fly ash to a thermoplastic polyester resin for improvement of the mechanical strength of thermoplastic polyester resin. In JP-A-2000-336254 is disclosed a polyester resin composition composed of 30 to 99 parts by weight of a thermoplastic polyester resin and 70 to 1 parts by weight of fly ash. The fly ash described therein has a specific surface area of 1,000 to 8,000 cm² μg.

Inorganic particles including the commercial fly ash disclosed in JP-A-2000-336254 have a D50 exceeding 10 μm. Incidentally, D50 is a particle size at a point where the integrated value of particles having diameters up to that diameter becomes 50 weight % of the total particles. In the present invention, the D50 of the inorganic particles used therein is controlled at 10 μm or less by classification or the like and, owing to the synergistic effect of such inorganic particles and a polycarbonate type resin, stable superior flame retardancy has been achieved for the first time with the reduction in moldability being suppressed.

Effects of the Invention

In the present invention, for a flame-retardant resin composition using a polycarbonate type resin and inorganic particles, the inorganic particles contain at least a complex of silicon dioxide and aluminum oxide and the particle sizes of the inorganic particles are controlled in a particular range; therefore; superior flame retardancy can be stably realized.

BRIEF DESCRIPTION OF THE DRAWINGS

FIG. 1 is a graph showing a relation between D50 of fly ash and flame retardancy.

FIG. 2 is a graph showing a relation between amount of fly ash used and flame retardancy.

FIG. 3 is a graph showing the particle size distribution of fly ash (FA-A4).

FIG. 4 is a graph showing the particle size distribution of fly ash (FA-A5).

BEST MODE FOR CARRYING OUT THE INVENTION

Figure 5:
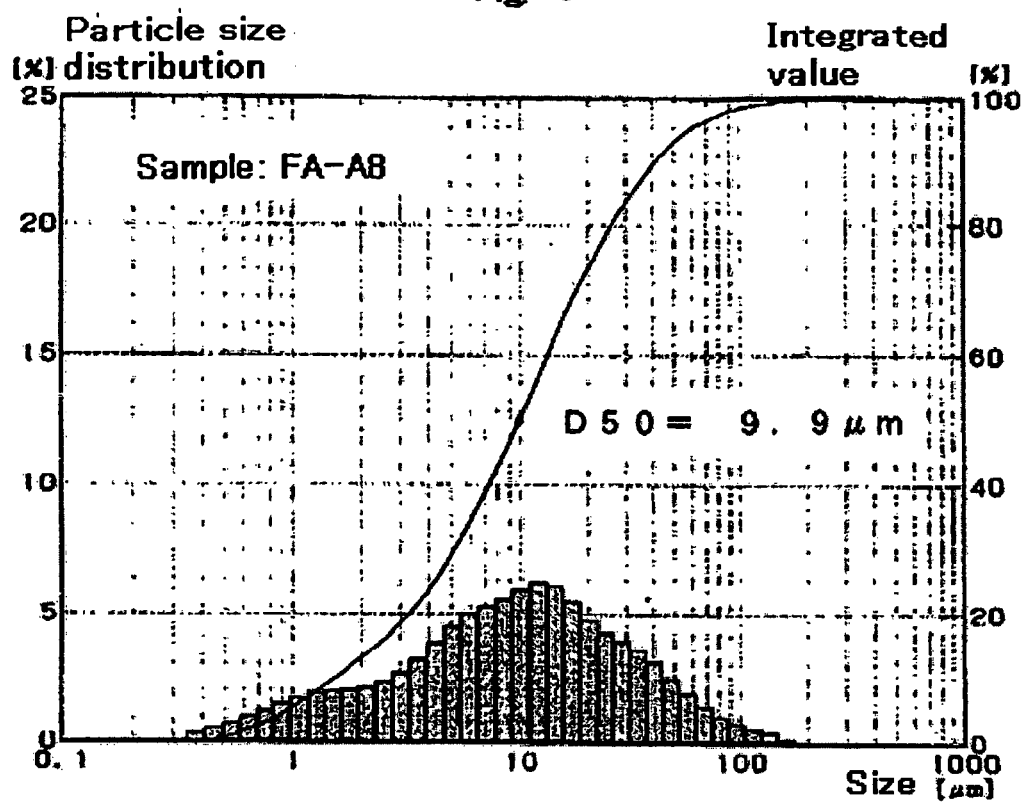
FIG. 5 is a graph showing the particle size distribution of fly ash (FA-A8).

The embodiment of the present invention is described in more detail below.

The flame-retardant resin composition in the present invention is compounded inorganic particles of particular particle size range with a polycarbonate type resin, and is characterized in that the inorganic particles contain a complex of silicon dioxide and aluminum oxide. By such a constitution, the polycarbonate type resin composition has improved flame retardancy and retains the moldability of the polycarbonate type resin.

The polycarbonate type resin in the present invention is a resin having a recurring unit represented by the following general formula (I).

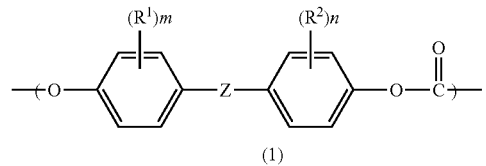

[Chemical formula 1]

(1)

(wherein, $R^1$ and $R^2$ are each an alkyl group of 1 to 6 carbon atoms or an aryl group of 6 to 12 carbon atoms and may be the same or different from each other; m and n are each an integer of 0 to 4; and Z is a single bond, an alkylene or alkylidene group of 1 to 6 carbon atoms, a cycloalkylene or cycloalkylidene group of 5 to 20 carbon atoms, a fluorenylidene group, or a —O—, —S—, —SO—, —SO$_2$— or —CO— bond).

The polycarbonate resin is a polymer produced, for example, by a phosgene method wherein a dihydroxydiaryl compound is reacted with phosgene and an ester exchange method wherein a dihydroxydiaryl compound is reacted with a carbonic acid ester (e.g. diphenyl carbonate), and is typified by a polycarbonate type resin produced from 2,2-bis(4-hydroxyphenyl)propane (bisphenol A).

As the dihydroxydiaryl compound, there can be mentioned, besides bisphenol A, bis(hydroxyaryl)alkanes such as bis(4-hydroxyphenyl)methane, 1,1-bis(4-hydroxyphenyl)ethane, 2,2-bis(4-hydroxyphenyl)butane, 2,2-bis(4-hydroxyphenyl)octane, bis(4-hydroxyphenyl)phenylmethane, 2,2-bis(4-hydroxy-3-methylphenyl)propane, 2,2-bis(4-hydroxy-3-tert-butylphenyl)propane, 2,2-bis(4-hydroxy-3-bromophenyl)propane, 2,2-bis(4-hydroxy-3,5-dibromophenyl)propane, 2,2-bis(4-hydroxy-3,5-dichlorophenyl)propane and the like; bis(hydroxyaryl)cycloalkanes such as 1,1-bis(4-hyroxyphenyl)cyclopentane and 1,1-bis(4-hydroxyphenyl)cyclohexane; dihydroxydiaryl ethers such as 4,4'-dihydroxydiphenyl ether and 4,4'-dihydroxy-3,3'-dimethyldiphenyl ether; dihydroxydiaryl sulfides such as 4,4'-dihydroxydiphenyl sulfide; dihydroxydiaryl sulfoxides such as 4,4'-dihydroxydiphenyl sulfoxide and 4,4'-dihydroxy-3,3'-dimethyldiphenyl sulfoxide; dihydroxydiarylsulfones such as 4,4'-dihydroxydiphenylsulfone and 4,4'-dihydroxy-3,3'-dimethyldiphenylsulfone; and so forth.

These dihydroxydiaryl compounds can be used singly or in mixture of two or more kinds. Use of a compound having no halogen substituent is preferred, because halogen-containing gas is not emitted to the environment during its combustion.

Together with the dihydroxydiaryl compound may be used piperazine, dipiperidyl hydroquinone, resorcin, 4,4'-dihydroxydiphenyl, hydroquinone, etc.

Together with the dihydroxydiaryl compound may also be used a phenolic compound which is trihydric or more, such as phloroglucin, 4,6-dimethyl-2,4,6-tris(4-hydroxyphenyl)heptene, 2,4,6-dimethyl-2,4,6-tris(4-hydroxyphenyl)heptane, 1,3,5-tris(4-hydroxyphenyl)benzene, 1,1,1-tris(4-hydroxyphenyl)ethane and 2,2-bis[4,4-di(4-hydroxyphenyl)cyclohexyl]propane.

The polycarbonate type resin preferably has a number-average molecular weight of 10,000 to 100,000.

When the number-average molecular weight of the polycarbonate type resin is 10,000 or more, there can be stably obtained a resin composition superior in mechanical strength and flame retardancy. When the number-average molecular weight of the polycarbonate type resin is 100,000 or less, the resulting resin composition has an appropriate viscosity range and accordingly good moldability.

The polycarbonate type resin in the present invention can be produced from the above-mentioned raw materials by a known method, if necessary, using a molecular modifier, a catalyst, etc.

In the present invention, there is no particular restriction as to the water content of the polycarbonate type resin, but the water content is preferably 1,000 ppm or less, for example. When the water content is in this range, the resin composition is produced more stable.

The content of the polycarbonate type resin is preferably 10 weight % or more, more preferably 40 weight % or more, further preferably 60 weight % or more relative to the total amount of the flame-retardant resin composition, and preferably 99 weight % or less, more preferably 95 weight % or less, further preferably 80 weight % or less. By adopting such content, together with the action of inorganic particles, superior flame retardancy is provided.

The inorganic particles used in the present invention mean particles composed mainly of inorganic components, and include also inorganic particles containing a small amount of organic components.

The inorganic particles used in the present invention are particles containing a complex of silicon dioxide and aluminum oxide. Herein, the complex of silicon dioxide and aluminum oxide means particles having a silicon dioxide phase and an aluminum oxide phase. As specific forms thereof, there can be mentioned, for example, particles containing a compound oxide of silicon and aluminum, and particles in which silicon dioxide particles and aluminum oxide particles have been fused each other.

By using inorganic particles having such a constitution, there can be realized superior flame retardancy which is not achieved by using silicon dioxide particle alone, aluminum oxide particles alone or a mere mixture thereof.

Preferably, the inorganic particles contain, in addition to the above complex particles, aluminum oxide particles and silicon dioxide particles. By using such inorganic particles containing several different kinds of particles, there can be stably obtained a flame-retardant resin composition of superior flame retardancy.

As inorganic particles having such a constitution, there can be mentioned, for example, particles containing a compound oxide of silicon and aluminum, and inorganic particles composed of a mixture of silica particles and alumina particles.

Such inorganic particles of low cost are not particularly restricted and there can be mentioned, for example, fly ash.

The incinerated ash obtained from incinerator or the like is a combustion ash obtained by combustion of various wastes. Meanwhile, the fly ash is a coal combustion ash which is generated in the coal combustion boiler of thermal power plant; since the composition of coal is known clearly, the fly ash is low in the content of heavy metals, etc. other than silicon and aluminum, as compared with the combustion ash generated in incinerator. Also in the fly ash, it is relatively easy to control the content of heavy metals, etc. Therefore, when the fly ash is added into a resin composition as filler, there is an advantage that the fly ash is unlikely to give an adverse effect on the environment.

The flame-retardant resin composition in the present invention has sufficient flame retardancy without containing a flame retardant such as phosphorus compounds, halogenated compounds or the like. No use of any phosphorus compounds or any halogenated compounds is preferred from the standpoint of environmental protection.

In the present invention, the D50 of the inorganic particles is preferably 1 μm or more, more preferably 3 μm or more. The D50 is preferably 10 μm or less, more preferably 7 μm or less.

When the D50 is 1 μm or more, the resin composition has improved flame retardancy and the reduction in moldability of the resin composition can be suppressed. Further, the scattering of the inorganic particles can be suppressed and the workability and handling stability in production of the resin composition are improved.

When the D50 is 3 μm or more, the resin composition has even higher flame retardancy. Also, the scattering of the inorganic particles is suppressed further and the workability and handling stability in production of the resin composition are improved further.

When the D50 is 10 μm or less, the resin composition has improved flame retardancy and the reduction in moldability of the resin composition can be suppressed. When the D50 is 7 μm or less, the carbonization of polycarbonate type resin during combustion is promoted further, which allows the resin composition to have even higher flame retardancy.

In the resent invention, the inorganic particles satisfy the above particle size requirement for D50, and are desired to further satisfy the following particle size requirement.

Desirably, the inorganic particles contain particles having particle sizes of 20 μm or less, in an integrated value of preferably 70% or more, more preferably 90% or more. When the proportion of the particles having particle sizes of 20 μm or less is 70% or more relative to the total inorganic particles, improved flame retardancy is obtained. Moreover, the reduction in moldability of resin composition is suppressed. When the proportion of the particles having particle sizes of 20 μm or less is 90% or more, further improved flame retardancy is obtained. Moreover, the reduction in moldability of resin composition is suppressed further.

The particle sizes of the inorganic particles can be measured by, for example, a method of observing the section of a molded article obtained from a resin composition, using an electron microscope.

Specifically explaining, an ultra-thin slice of a resin composition is observed using a transmission type electron microscope, or a surface of a cut-out resin composition sample is observed using a scanning type electron microscope; a photograph is taken; using the photograph, there are measured the sizes of 100 or more individual particles in the resin composition. Incidentally, the size of each particle is determined by measuring the area (S) of the particle and making calculation from $(4\,S/p)^{1/2}$. The sizes of the inorganic particles can also be measured by a light-scattering method (described later) and a substantially equivalent value is obtained.

In the present invention, it is preferred that the content of total silicon dioxide in inorganic particles is 44 to 85 weight % relative to the total amount of inorganic particles and that the content of total aluminum oxide is 15 to 40 weight %. It is also preferred that the total content of total silicon dioxide and total aluminum oxide in inorganic particles is 60 weight % or more relative to the total amount of inorganic particles. It is preferred that the silicon dioxide and the aluminum oxide are contained in the inorganic particles in the form of a complex. For example, in fly ash, mullite (which is a complex of silicon dioxide and aluminum oxide) is contained by 3 to 45 weight % ["Coal Ash Handbook" 2000, Environmental Technology Association and Japan Fly Ash Association]. Hence, fly ash is preferred also from this point.

In the present invention, there is no particular restriction as to the content of inorganic particles in flame-retardant resin composition. However, the content of inorganic particles is preferably 1 weight % or more, more preferably 5 weight % or more, further preferably 20 weight % or more, relative to the total resin composition. Also, the content of inorganic particles is preferably 60 weight % or less, more preferably 50 weight % or less, further preferably 40 weight % or less.

When the content of inorganic particles is 1 weight % or more, the resin composition can have improved flame retardancy stably and the reduction in moldability of resin composition can be suppressed stably. When the content of inorganic particles is 5 weight % or more, the resin composition can have improved flame retardancy more stably. When the content of inorganic particles is 10 weight % or more, the resin composition can have even higher flame retardancy.

When the content of inorganic particles is 65 weight % or more, injection molding tends to be difficult. However, when the content is 60 weight % or less, the resin composition has good injection-moldability and good flame retardancy. When the content of inorganic particles is 50 weight % or less, the proportions of resin component and inorganic particles in resin composition are appropriate and improved flame retardancy is obtained. Also, molding of resin composition is easier. When the content of inorganic particles is 40 weight % or less, the flame retardancy of resin composition is even higher and the moldability of resin composition is better.

In the present invention, it is preferred to use, as the inorganic particles, fly ash (hereinafter abbreviated to "FA", appropriately).

FA is a fine powder of coal combustion ash, which is collected by a dust collector in a thermal power plant and the like where coal is burnt by a pulverized coal combustion method.

FA typically contains the following components.
(a) Silicon dioxide: 44 to 80 weight %
(b) Aluminum oxide: 15 to 40 weight %
(c) Other components: ferric oxide ($Fe_2O_3$), titanium oxide ($TiO_2$), magnesium oxide (MgO), calcium oxide (CaO) and the like In the FA used in the present invention, the content of silicon dioxide (silica: $SiO_2$) is preferably 44 weight % or more, more preferably 50 weight % or more. Also, the content is preferably 85 weight % or less, more preferably 75 weight % or less. When the content of silicon dioxide is in this range, the resin composition can have improved flame retardancy stably owing to the synergistic effect between inorganic particles and polycarbonate type resin composition.

Meanwhile, the content of aluminum oxide (alumina: $Al_2O_3$) is preferably 10 weight % or more, more preferably 15 weight % or more. Also, the content is preferably 40 weight % or less, more preferably 30 weight % or less. When the content of aluminum oxide is in this range, the resin composition can have improved flame retardancy stably owing to the synergistic effect between inorganic particles and polycarbonate type resin composition.

In the FA used in the present invention, the total content of silicon dioxide and aluminum oxide is preferably 60 weight % or more, more preferably 70 weight % or more, further preferably 80 weight % or more. Also, the total content of silicon dioxide and aluminum oxide is preferably 99 weight % or less, more preferably 95 weight % or less. When the total content of silicon dioxide and aluminum oxide is in this range, the resin composition can have improved flame retardancy stably owing to the synergistic effect between inorganic particles and polycarbonate type resin composition.

In the FA, silicon dioxide and aluminum oxide partly form a compound oxide and partly form particles having a multiphase structure composed of a silicon dioxide phase and an aluminum oxide phase.

In the FA, ferric oxide ($Fe_2O_3$), titanium oxide ($TiO_2$), magnesium oxide (MgO) and calcium oxide (CaO) do not deteriorate the flame retardancy, moldability, etc. of resin composition as long as the contents of silicon dioxide and aluminum oxide are in the above-mentioned ranges. The FA contains, besides these oxides, a small amount of heavy metals, etc.; however, the concentration of heavy metals, etc. is low as compared with the level in the incineration ash obtained from incinerator, etc. The reason therefor is that while the incineration ash is a combustion ash obtained by burning various kinds of wastes, the FA is a coal combustion ash generated at thermal power plants.

Since the FA is produced from a raw material of known composition, it is relatively easy in the FA to control the content of heavy metals, etc. By applying a preventive measure for elution of a small amount of heavy metals, etc., the adverse effect of resin composition or molded article thereof, on environment can be reduced further.

In the FA, a majority of particles have a spherical shape when observed by an electron microscope. Therefore, by using the FA, it is possible to suppress the reduction of moldability in molding of resin composition and further improve the flame retardancy of resin composition.

Currently, the FA is generated in thermal power plants etc. in a large amount and the most part thereof is treated as an industrial waste. Therefore, the FA is low in cost, making it possible to produce a flame-retardant resin composition at a low cost.

FIG. 3 is a graph showing the particle size distribution of a FA (A4) shown in Table 1 given later.

In this FA-A4, the D50 is 3.9 μm, the integrated value of particles having sizes of 20 μm or less are 97%, and the integrated value of particles having sizes of 0.5 μm or more are 96%. The FA-A4 has two particle size distribution peaks at about 1.5 μm and at about 6.0 μm, that is, has a unique bimodal distribution.

When the FA has such two peaks in its particle size distribution, the resin composition containing the FA has good flame retardancy stably. Further, in the resin composition, the reduction in moldability is suppressed stably.

In commercial FA, the D50 is usually more than 10 μm; therefore, it is unable to use the commercial FA itself in the present invention. Hence, it is preferred to use a FA obtained by subjecting the commercial FA to particle size control by classification or the like. Thereby, a striking synergistic effect is obtained between polycarbonate type resin and inorganic particles and superior flame retardancy can be realized stably. Further, the resin composition can keep good moldability.

Incidentally, as the method for particle size control of inorganic particles, there are classification using a sieve having a particular opening, classification using an air-current classifier, and the like.

When the resin composition containing inorganic particles such as FA is used as a molded article, there is a possibility that a small amount of heavy metals, etc. are eluted from the molded article, depending upon the environment or method in which the molded article is used. Incidentally, in the present invention, "heavy metals, etc." are a total of heavy metals such as chromium (VI), lead and silver and harmful elements such as selenium and arsenic.

In the flame-retardant resin composition of the present invention, when FA is used as the inorganic particles, a measure which prevents to be eluted a very small amount of heavy metals, etc. may be employed as long as it does not hurt to the properties and appearance of the flame-retardant resin composition.

As the measure preventing for the elution of heavy metals, etc., there can be taken, for example, a method of adding an elution preventer to the present resin composition and a method of forming, on the surface of the present resin composition molded article, a film having a preventability for elution (for example, applying a coating containing an elution preventer on the surface).

By employing the measure preventing for elution, the elution of heavy metals, etc. can be suppressed reliably even when the content of heavy metals, etc. varies slightly depending upon the kind of coal (which is a raw material for FA), the combustion conditions when FA is produced, etc. Further, since FA can be used regardless of the content-level of heavy metals, etc., FA (which is a by-product of thermal power plants) can be utilized more effectively as a resource.

As the measure preventing for the elution of heavy metals, etc., the method of adding an elution preventer to the present resin composition is simple and moreover effective in long-term use.

As the elution preventer for heavy metals, etc., there can be mentioned an adsorbing agent or a reducing agent both using an inorganic compound, an ion exchange resin, etc.

As the adsorbing agent or the reducing agent both using an inorganic compound, there can be mentioned, for example, ferrous or ferric sulfate, Schwertmannite, sodium thiosulfate, hydrotalcite and hydroxyapatite. Ferrous sulfate and Schwertmannite are preferred particularly.

As the ion exchange resin, there can be mentioned chelate resins, anion exchange resins, cation exchange resins, etc.

As the effect of such an elution preventer, there can be mentioned that adsorbing agent adsorbs heavy metals, etc by forming an adsorbent (e.g. hydrate of metal oxide of metal such as iron or the like) in resin, or that reducing agent reduces and makes insoluble heavy metals, etc. There are cases that, when reducing agent and adsorbing agent is used in combination, heavy metals, etc. are reduced and made more adsorbable. Therefore, an adsorbing agent and a reducing agent may be used in admixture.

The elution preventer is often a hydrate compound such as ferrous sulfate mono-hydrate. Therefore, when it is added in excess, water vaporizes in injection molding of resin composition and there may arise the generation of silvery streaks (hereinafter referred to as "silver") on the surface of molded article or the color change of molded article caused by the elution preventer, which reduces the appearance of molded article.

Therefore, the addition amount of the elution preventer is preferably at most less than 2 weight %, more preferably 1 weight % or less.

When FA is used as the inorganic particles, the elution preventer can prevent the elution of heavy metals, etc. when used at $1/1000$ or more, particularly preferably at $1/100$ or more in terms of weight ratio to FA. For example, when the present resin composition contains FA in an amount of 10 weight %, the desired addition level of the elution preventer is 0.01 weight % or more, preferably 0.1 weight % or more and less than 2 weight %. Thereby, the generation of inferior appearance (e.g. silver) can be suppressed and also the elution of heavy metals, etc. can be prevented.

When there is formed, on the surface of the molded article of resin composition, a film having a preventability for elution, there can be employed a method of covering the surface of the molded article with a water-repellent film or a water-non-permeable film. There is no particular restriction as to the water-repellent film but, for example, a fluororesin type film can be used. Combination use of such a film and an elution preventer is more effective for the prevention of the elution of heavy metals, etc.

In the present invention, the resin composition containing a polycarbonate type resin and inorganic particles is preferred to further contain a fiber-formable fluorinated polymer which can form a fiber structure (a fibril structure) in the resin composition. By using a fiber-formable fluorinated polymer, a dripping phenomenon during combustion can be prevented.

As the fiber-formable fluorinated polymer, there can be mentioned polytetrafluoroethylene, tetrafluoroethylene-based copolymer (e.g. tetrafluoroethylene/hexafluoropropylene copolymer), partially fluorinated polymer, polycarbonate produced from fluorinated diphenol, etc.

As the fiber-formable fluorinated polymer, there can also be used fluoropolymers in various forms, such as fine powder state of fluoropolymer, aqueous dispersion of fluoropolymer, powder state of fluoropolymer/acrylonitrile-styrene copolymer mixture, powder state of fluoropolymer/polymethylmethacrylate mixture, and the like.

The appropriate addition amount of the fiber-formable fluorinated polymer is preferably 0.05 weight % or more, more preferably 0.1 weight % or more based on the total flame-retardant resin composition. Also, the appropriate addition amount is preferably 5 weight % or less, more preferably 1 weight % or less, further preferably 0.8 weight % or less.

When the addition amount of the fiber-formable fluorinated polymer is 0.05 weight % or more, the effect of preventing the dripping during combustion is obtained stably. When the addition amount of the fiber-formable fluorinated polymer is 0.1 weight % or more, the resin composition has higher flame retardancy.

When the addition amount of the fiber-formable fluorinated polymer is 5 weight % or less, the polymer is dispersed in the resin easily; as a result, the polymer can be easily mixed homogeneously with the polycarbonate type resin, making possible the stable production of a flame-retardant resin composition. When the addition amount of the fiber-formable fluorinated polymer is 1 weight % or less, the resin composition has higher flame retardancy. When the addition amount of the fiber-formable fluorinated polymer is 0.8 weight % or less, the resin composition has even higher flame retardancy.

The reason why a polycarbonate type resin-containing resin composition exhibits flame retardancy by compounding therein inorganic particles (e.g. FA) containing particles containing silicon dioxide and aluminum oxide, is presumed to be as follows.

Polycarbonate type resin has carbonate bond in its chemical structure; the oxygen in this carbonate bond forms hydrogen bond with the hydroxyl group at the surface of inorganic particles; thereby, the polycarbonate type resin is stabilized thermally. With inorganic particles having a particular particle size range, the degree of forming hydrogen bond with polycarbonate type resin is higher and, during combustion, there is easily formed a composite between inorganic particles and polycarbonate type resin, which promotes carbonization and resultantly enhances flame retardancy strikingly.

Further, it is considered that the complex of silicon dioxide and aluminum oxide, present in inorganic particles uniquely acts as a flame-retardant catalyst toward the polycarbonate type resin. When, in particular, FA is used, the organic components on the surface of molded article vaporize at the initial stage of combustion and the surface contains a high-concentration of FA or becomes a polycarbonate-FA composite material; this also is considered to contribute to high flame retardancy.

In the present invention, there may be added, to the flame-retardant resin composition, various additives (e.g. thermal stabilizer, anti-oxidant, coloring agent, fluorescent whitening agent, filler, release agent, softening agent, anti-static agent, plasticizer and dispersing agent), impact resistance improver, other polymer, etc. as long as the effect of the flame-retardant resin composition is not impaired. Further, the inorganic particles (e.g. FA) may be surface-treated with silane type coupling agent, titanate type coupling agent, etc.

As the thermal stabilizer, there can be mentioned, for example, metal hydrogensulfates such as sodium hydrogensulfate, potassium hydrogensulfate and lithium hydrogensulfate; and metal sulfates such as aluminum sulfate. They can be used ordinarily in an amount of 0 to 0.5 weight %.

As the filler, there can be mentioned, for example, glass fiber, glass beads, glass flake, carbon fiber, talc powder, clay powder, mica, potassium titanate whiskers, wollastonite powder and the like.

As the impact resistance improver, there can be mentioned, for example, glass fiber, organic fiber, acrylic type elastomer, polyester type elastomer, methyl methacrylate-butadiene-styrene copolymer in the form of core-shell type, methyl methacrylate-acrylonitrile-styrene copolymer, ethylene-propylene-based rubber, ethylene-propylene-diene-based rubber and the like. Particularly, glass fiber is superior in properties as impact resistance improver.

As the plasticizer, there can be mentioned, for example, trimellitic acid ester, pyromellitic acid ester, polycarbonate diol, trimethylolpropane tribenzoate, dipentaerythritol, polycaprolactone, p-hydroxybenzoic acid alkyl ester and the like.

As the dispersing agent, there can be mentioned, for example, olefin-maleic acid copolymer, styrene-maleic anhydride copolymer, sodium naphthalenesulfonate and the like.

Other flame retardants may be added, if necessary. As such, there can be mentioned phosphorus compounds, heat-absorbing agent (e.g. metal hydroxide or boric acid salt), nitrogen compound (e.g. melamine), silicone-based flame retardant, carbonization-promoting agent (e.g. metal salt), halogenated compounds, etc.

In the present invention, there is no particular restriction for the method for producing the present resin composition. As the method, there can be mentioned mixing using a known mixer such as tumbler, ribbon blender, Banbury mixer or kneader, or melt kneading using a known extruder such as single-screw extruder or twin-screw extruder.

There can be shown, for example, a method which comprises separately preparing a premix of raw materials composed of pellet-like components (e.g. resin component) and a premix of raw materials composed of powdery components (e.g. inorganic particles including FA, etc.), feeding the premixes independently into an extruder, and conducting melt kneading, and a method which comprises feeding raw materials each independently into an extruder and conducting melt kneading.

The present resin composition can also be obtained by producing, using a mixer, a master batch wherein inorganic particles have been dispersed in an organic solvent, a molten resin or the like, and compounding this master batch at the time of molding of a resin composition.

This method is effective particularly when the particle sizes of inorganic particles are small, because the production of master batch can suppress the scattering of inorganic particles and can give enhanced workability and handling stability.

In the melt kneading, the cylinder temperature of extruder may be set at 200 to 400° C., preferably at 220 to 350° C., more preferably at 230 to 300° C. The screw rotation of extruder can be set at 30 to 700 rpm, preferably at 80 to 500 rpm, more preferably at 100 to 300 rpm.

In the melt kneading, the average residence time in extruder can be set at 10 to 150 seconds, preferably at 20 to 100 seconds, more preferably at 30 to 60 seconds. The temperature of resin composition melt is set at a range of preferably 250 to 300° C., and the melt kneading can be conducted with attention being paid so that no excessive heat is applied to the resin composition during kneading. The melt-kneaded resin composition is extruded from the die fitted to the front end of extruder, as a strand and is pelletized, whereby resin composition pellets can be obtained.

In the production of the present flame-retardant resin composition, it is possible to conduct degassing simultaneously with melt kneading. The degassing means that the volatile components generated in the melt kneading step are removed under atmospheric pressure or reduced pressure through the vent fitted to the extruder.

The flame-retardant resin composition pellets obtained thus have high flame retardancy and therefore can be used as a flame-retardant molding material for formation of molded articles used in electric or electronic appliance application, building material application, automobile part application, daily good application, medical care application, agricultural application, toy, pleasure goods, etc.

In the present invention, there is also provided a flame-retardant molding material containing the above-mentioned flame-retardant resin composition.

Incidentally, herein, the flame-retardant resin molding material means a resin molding material having such a property that the combustion of resin composition is suppressed even in a high-temperature oxidizing atmosphere. A typical example thereof is resin composition pellets composed of a flame-retardant resin composition.

The flame-retardant resin composition of the present invention is useful as a composition capable of giving enhanced flame retardancy. By suitably compounding this flame-retardant resin composition into a thermoplastic resin or the like, a flame-retardant molding material can be obtained. Therefore, the flame-retardant molding material of the present invention may be a material composed only of the above-mentioned flame-retardant resin composition, or may contain a thermoplastic resin other than polycarbonate type resin in order to further improve the moldability (e.g. melt fluidity) and mechanical properties (e.g. impact resistance).

As such a thermoplastic resin, there can be used one kind or a combination of two or more kinds, selected from, for example, polystyrene type resins such as polystyrene, high-impact polystyrene, styrene-butadiene copolymer rubber and the like; polyphenylene ether type resins; polyolefin type resins; polyvinylchloride type resins; polyamide type resins; polyester type resins; polypropylene type resins; polyphenylene sulfide type resins; polymethacrylate type resins; rubber-modified polymers; polyacrylate type resins; acrylonitrile-butadiene copolymer rubber; acrylonitrile-styrene copolymer and acrylic rubber-modified product thereof; and styrene-based polymers such as acrylonitrile-butadiene-styrene copolymer, acrylonitrile/ethylene-propylene-diene-based rubber (EPDM)/styrene copolymer, and the like.

Of these thermoplastic resins, preferred are polybutadiene, styrene-butadiene copolymer rubber, acrylonitrile-butadiene copolymer rubber, polybutyl acrylate, etc.

In the present invention, there is no particular restriction as to the proportion of the flame-retardant resin composition in the flame-retardant molding material; however, the proportion is preferably 10 weight % or more, more preferably 30 weight % or more, further preferably 60 weight % or more and preferably 99 weight % or less, more preferably 85 weight % or less, further preferably 70 weight % or less.

When the proportion of the flame-retardant resin composition is 10 weight % or more, the flame-retardant molding material containing the resin composition shows a small reduction in moldability and yet has enhanced flame retardancy stably. When the proportion of the flame-retardant resin composition is 30 weight % or more, the flame-retardant molding material has a good balance between the flame retardancy and the moldability.

When the proportion of the flame-retardant resin composition is 60 weight % or more, the flame-retardant molding material has a better balance between the flame retardancy and the moldability.

When the proportion of the flame-retardant resin composition is 99 weight % or less, the flame-retardant molding material containing the resin composition tends to be superior in mechanical strengths and moldability. When the proportion of the flame-retardant resin composition is 85 weight % or less, the flame-retardant molding material has a good balance between the flame retardancy and the moldability. When the proportion of the flame-retardant resin composition is 75 weight % or less, the flame-retardant molding material has a better balance between the flame retardancy and the moldability.

In the present invention, there can be provided a molded article containing the above-mentioned flame-retardant resin composition. According to this constituent, the molded article is superior in flame retardancy and shows a small reduction in moldability.

As to the method for molding the above-mentioned flame-retardant molding material, there is no particular restriction, and there can be used known methods such as injection molding, gas-assisted molding, extrusion molding, blow molding, injection and compression, and the like.

The molded article obtained by such a method has superior flame retardancy; therefore, it can be used in electric or electronic appliance application, building material application, automobile part application, daily good application, medical care application, agricultural application, toy, pleasure goods, etc. Particularly, the molded article is suitably used in the casing for electric or electronic appliances in which superior flame retardancy is required.

The constitutions of the present invention have been described above. Any combination of these constitutions is also useful as an embodiment of the present invention.

EXAMPLES

The present invention is described further by way of Examples. However, the present invention is not restricted thereby.
(1) Method for Measurement of Particle Size Distribution Particle size distribution of inorganic particles was measured by the light-scattering method using a particle size distribution tester "D.H.S 9200PRO Type FRA" produced by MICRO TRAC CO., under the following conditions.

Dispersing medium: a 2 weight % aqueous sodium hexametaphosphate solution (refractive index: 1.33)

Measurement time: 20 seconds, 3 times

Pretreatment: about 20 mg of a sample was placed in 30 ml of a dispersing medium and subjected to a dispersing treatment for 3 minutes using an ultrasonic wave (20 kHz, 300 kW), the resulting dispersion was placed in a measurement cell, and adjustment was made using pure water to obtain a concentration of 0.1 g/liter.
(2) Raw Materials Used
(2-1) Thermoplastic Resins PC: a polycarbonate type resin [a product of Sumitomo Dow Ltd., trade name: Calibre 301-22 (weight-average molecular weight: 47,000, number-average molecular weight: 27,000)]

PET: a polyethylene terephthalate (a product of TOYOBO Co., Ltd., trade name: PETMAX RE554)

PBT: a polybutylene terephthalate (a product of Mitsubishi Engineering Plastics K.K., trade name: NOVADURAN 5010 R5)

PP: a polypropylene (a product of Sumitomo Chemical Co., Ltd., trade name: AH561)

Ny: a 6-nylon (a product of Toray Industries, Ltd., trade name: Amilan CM1017)
(2-2) Inorganic Particles FA: fly ash. Products shown in the following Table 1 were used.

Some of the FA's shown in Table 1 were measured for particle size distribution and the results are shown in FIGS. 3 to 8.

Incidentally, FA's A4 to A7 correspond to Type I fly ash specified in JIS A 6201 (1999) and are suited for achievement of flame retardancy, and FA's A8 to A12 correspond to Type II flay ash (standard) specified therein and have relatively large particle sizes.

FA-A8 is a product of Type II fly ash; however, since it has a small D50 of 9.9 μm, enhanced flame retardancy was obtained.

The FA's shown here were confirmed, by elemental analysis, to contain particles which were a complex of silicon dioxide and aluminum oxide, particles composed mainly of silicon dioxide, and particles composed mainly of aluminum oxide. Although being different depending upon the samples, the contents of mullite (a complex of silicon dioxide and aluminum oxide) in the FA's were 3 to 44 weight %.

S: a spherical silicon dioxide (a product of Denki Kagaku Kogyo K.K., trade name: FB3SCC, average particle size: 3.2 μm)

HS: a crushed silicon dioxide (a product of Denki Kagaku Kogyo K.K., trade name: FS3CC, average particle size: 3.2 μm)

Al: a spherical aluminum oxide (a product of Showa Denko K.K., trade name: CB-A05S, average particle size: 2.9 μm)
(2-3) Fiber-formable Fluorinated Polymer PTFE: a polytetrafluoroethylene (a product of Daikin Industries, Ltd., trade name: Polyflon FA-500, a fiber-formable fluorinated polymer)
(2-4) Elution Preventers FD-1: $FeSO_4 \cdot H_2O$ (ferrous sulfate monohydrate) (a product of Fuji Titanium Industry Co., Ltd., trade name: FD-1)

SW: Schwertmanite (a product of Sophia Co., trade name: Asre-S, chemical formula: $Fe_8O_8(OH)_{8-2x}(SO_4)_x \cdot nH_2O$ ($1 \leq x \leq 1.75$))
(3) Production of Resin Compositions and Resin Molded Articles A polycarbonate type resin (Calibre 301-22) and a FA were fed into a continuous kneading extruder (a product of KCK, KCK 0X2-35VVEX(7)) whose cylinder temperature had been set at 280° C., and was kneaded and extruded under melting and shear; then, the extrudate was cooled and solidified in water; and the solidified extrudate was cut into pellets.

The obtained pellets of each resin composition were dried at 120° C. for 4 hours and molded using a 20-ton injection molding machine (a product of Toshiba Machine Co., Ltd., EC20P-0.4A) under the conditions of cylinder temperature=280° C. and die temperature=80° C., whereby were

TABLE 1

Figure 6:
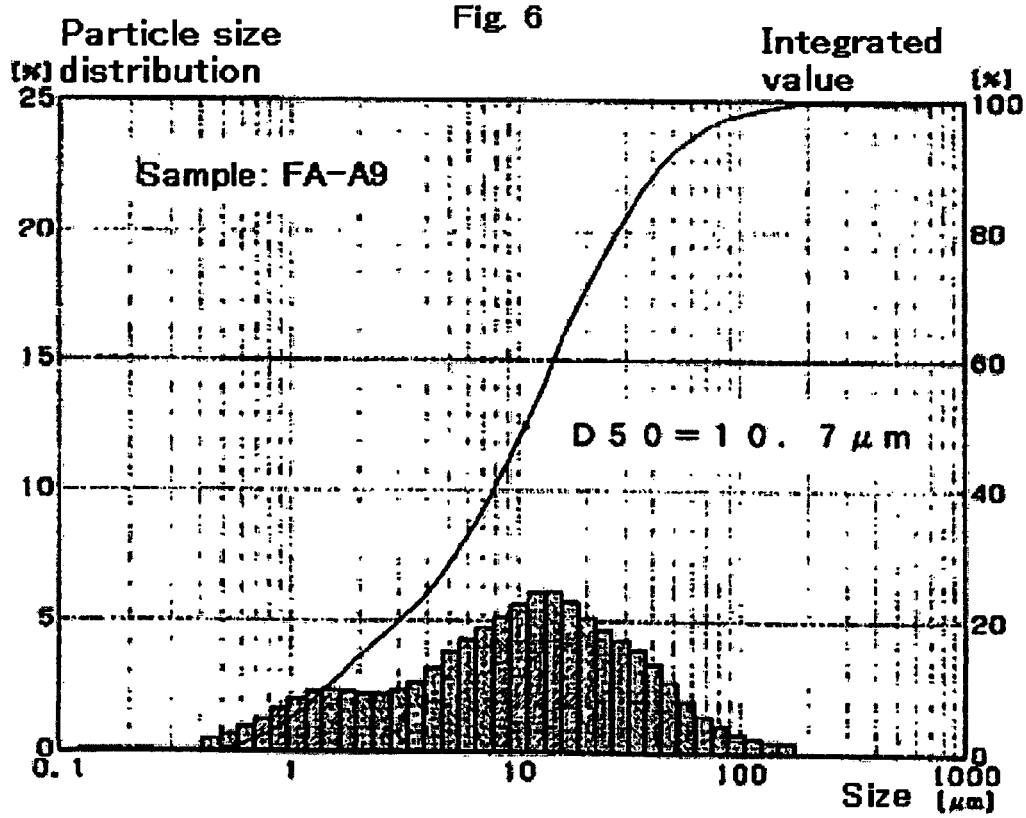
FIG. 6 is a graph showing the particle size distribution of fly ash (FA-A9).
Figure 7:
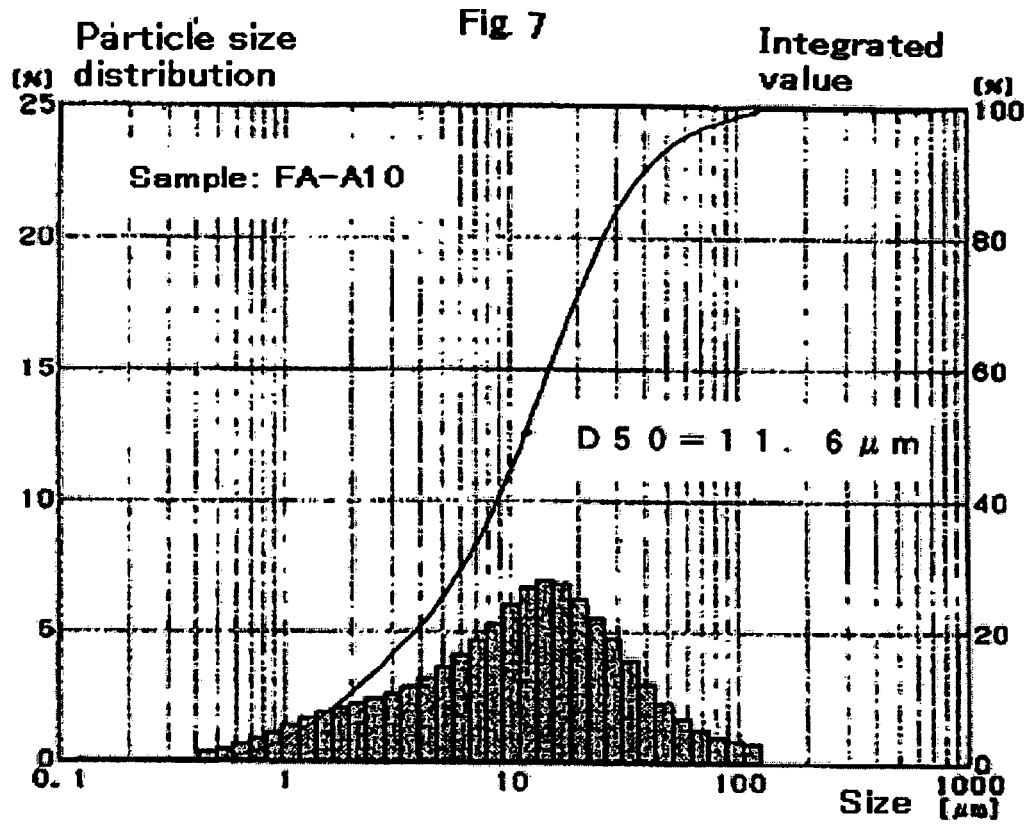
FIG. 7 is a graph showing the particle size distribution of fly ash (FA-A10).
Figure 8:
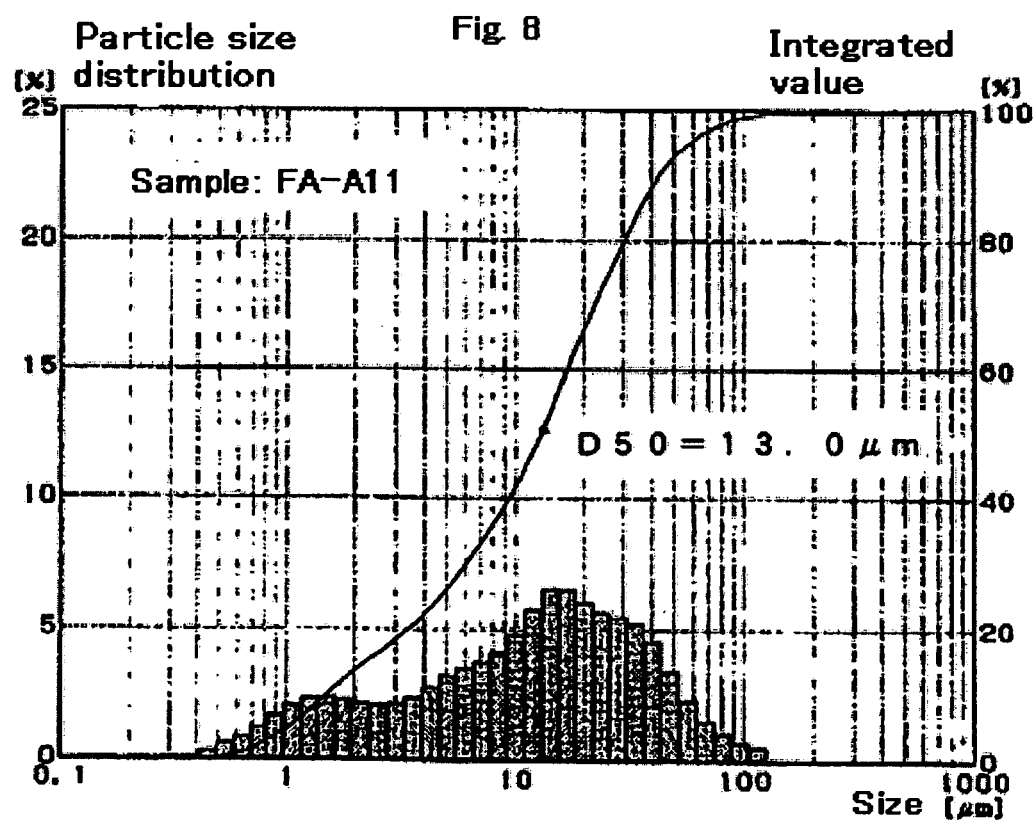
FIG. 8 is a graph showing the particle size distribution of fly ash (FA-A11).

| FA | Source | Proportion of particles of 20 μm or less in size weight % | D50 μm | Volume-average particle size μm | Content (weight %) | | | Graph of particle size distribution |
|---|---|---|---|---|---|---|---|---|
| | | | | | $SiO_2$ | $Al_2O_3$ | $SiO_2/Al_2O_3$ complex | |
| A1 | A5 classification | — | 0.6 | 0.6 | 63.7 | 20.6 | Present | — |
| A2 | A5 classification | — | 0.9 | 0.9 | 63.7 | 20.6 | Present | — |
| A3 | A5 classification | — | 1.2 | 1.1 | 63.7 | 20.6 | Present | — |
| A4 | Yonden Business | 97 | 3.9 | 3.2 | 72.1 | 17.2 | Present | FIG. 3 |
| A5 | Yonden Business | 96 | 5.0 | 5.2 | 63.7 | 20.6 | Present | FIG. 4 |
| A6 | Yonden Business | — | 6.4 | 6.4 | 54.2 | 26.4 | Present | — |
| A7 | Techno Chubu | — | 8.0 | 8.4 | 68.1 | 23.5 | Present | — |
| A8 | Kyushu Denryoku | 71 | 9.9 | 9.9 | 69.3 | 19.0 | Present | FIG. 5 |
| A9 | Yonden Business | 69 | 10.7 | 10.2 | 70.1 | 19.2 | Present | FIG. 6 |
| A10 | Denpatsu Coal Tech & Marine | 68 | 11.6 | 11.6 | 54.0 | 25.9 | Present | FIG. 7 |
| A11 | Techno Chubu | 63 | 13.0 | 13.8 | 62.8 | 23.1 | Present | FIG. 8 |
| A12 | Hokuriku Denryoku | — | 14.0 | 15.9 | 62.1 | 21.3 | Present | — | produced test pieces for flame-retardancy evaluation (125 mm×13 mm×1.6 mm), test pieces for oxygen index evaluation (125 mm×6.5 mm×3.0 mm) and test pieces for Flexural test evaluation (125 mm×12.7 mm×3.2 mm) of all the above resin compositions.

Exceptionally, the cylinder temperatures in kneading and injection were each 260° C. for the resin compositions containing a polyethylene terephthalate (PET), a polybutylene terephthalate (PBT), a polypropylene (PP) or a 6-nylon (Ny).

(4) Various Evaluations (4-1) Evaluation of Flame Retardancy

Oxygen index, which is an index for evaluation of flame retardancy, was measured for a test piece for oxygen index evaluation (125 mm×6.5 mm×3.0 mm) obtained by injection molding, according to JIS K 7201 (ISO 4589).

Evaluation of flame retardancy by UL 94 test was conducted by allowing a test piece for flame retardancy evaluation (125 mm×13 mm×1.6 mm) obtained by injection molding to stand for 48 hours in a thermostat chamber of 23° C. (temperature) and 50% (humidity) and then subjecting it to the UL 94 test (a combustion test for plastic material for apparatus part) specified by Underwriters Laboratories.

The UL 94 test is a method for evaluation of flame retardancy, which comprises contact a flame of burner with a test piece of given size held vertically, for 10 seconds and then examining the afterflame time and dripping property of the test piece. Flame retardancy is classified into the levels shown in the following Table 2.

TABLE 2

| Criteria Conditions | V-0 | V-1 | V-2 |
|---|---|---|---|
| Afterflame time after flame contact (each of 1st contact and 2nd contact) | ≦10 s | ≦30 s | ≦30 s |
| Total Afterflame time of 10 contacts of 5 samples | ≦50 s | ≦250 s | ≦250 s |
| Afterflame and reddening time after 2nd flame contact | ≦30 s | ≦30 s | ≦60 s |
| Sample which burns up to the position of fixing clamp | No | No | Yes |
| Ignition of cotton by drip | No | No | No |

Incidentally, flame retardancy was classified as a level "not V-2" when the mode of combustion was other than those classified in Table 2. The order of flame retardancy is V-0, V-1 and (V-2 and not V-2) with V-0 being the best.

In the above, "afterflame time" is a length of time in which the test piece after removal of ignition source continues flaming combustion; and "ignition of cotton by drip" means that the cotton as label located about 300 mm below the lower end of test piece is ignited by the drip dropped from the test piece.

(4-2) Evaluation of Mechanical Strength

A test piece for evaluation of Flexural test (125 mm×12.7 mm×3.2 mm) obtained by injection molding was measured for Flexural strength and Flexural modulus in accordance with ASTM C-256.

(4-3) Evaluation of Moldability

For evaluation of moldability, the melt fluidity of obtained resin composition was measured. A resin composition was dried at 120° C. for 4 hours; the dried composition was measured for spiral flow using a 20-ton injection molding machine (EC20P-0.4A, a product of Toshiba Machine Co., Ltd.), under the conditions of cylinder temperature=280° C., die temperature=80° C., injection pressure=1,600 kg/cm² and thickness=1 mm; and the melt flow property was evaluated based on the following standard.

○: Superior in melt flow property
Δ: Insufficient in melt flow property
X: Inferior in melt flow property Test Example 1

Flame Retardancy by Oxygen Index and Moldability

FA-A5 (D50=5.0 μm) was compounded into PC in a proportion shown in Table 3, to produce various flame-retardant resin compositions. A test piece for evaluation of oxygen index was produced from each composition and measured for oxygen index. Each composition was also examined for moldability. The results are shown in Table 3. For reference, the oxygen index and moldability for the PC per se are shown.

TABLE 3

| | Composition | | | | Evaluation | |
|---|---|---|---|---|---|---|
| | PC | Inorganic particles | | | Oxygen | |
| Run No. | weight % | Kind | D50 (μm) | weight % | index % | Moldability |
| 1 | 100 | — | — | — | 25 | ○ |
| 2 | 99.5 | FA-A5 | 5.0 | 0.5 | 25 | ○ |
| 3 | 99 | FA-A5 | 5.0 | 1 | 26 | ○ |
| 4 | 97 | FA-A5 | 5.0 | 3 | 28 | ○ |
| 5 | 70 | FA-A5 | 5.0 | 30 | 36 | ○ |
| 6 | 40 | FA-A5 | 5.0 | 60 | 42 | ○ |
| 7 | 35 | FA-A5 | 5.0 | 65 | — | X |

Test Example 2

Investigation of FA D50 Versus Flame Retardancy

PTFE and FA were compounded into PC in proportions shown in Table 4, to produce flame-retardant resin compositions. The compositions were evaluated for flame retardancy and average afterflame time by UL 94. The compositions were also examined for moldability. The results are shown in Table 4. Relations between D50 and average afterflame time are shown in FIG. 1. For reference, the results of the PC per se are shown.

TABLE 4

| | Composition | | | | | Evaluation | | |
|---|---|---|---|---|---|---|---|---|
| | PC | PTFE | Inorganic particles | | | Flame | Average | |
| Run No. | weight % | weight % | Kind | D50 (μm) | weight % | retardancy 1.6 mm | afterflame time s/sample | Moldability |
| 8 | 100 | 0 | — | — | — | V-2 | Drip | ○ |
| 9 | 99.5 | 0.5 | — | — | — | Not V-2 | >30 | ○ |
| 10 | 69.5 | 0.5 | FA-A1 | 0.6 | 30 | Not V-2 | >30 | Δ |
| 11 | 69.5 | 0.5 | FA-A2 | 0.9 | 30 | Not V-2 | >30 | Δ |
| 12 | 69.5 | 0.5 | FA-A3 | 1.2 | 30 | V-0 | 3.2 | ○ |
| 13 | 69.5 | 0.5 | FA-A4 | 3.9 | 30 | V-0 | 0.4 | ○ |

TABLE 4-continued

| | Composition | | | | | Evaluation | | |
|---|---|---|---|---|---|---|---|---|
| | PC | PTFE | Inorganic particles | | | Flame | Average | |
| Run No. | weight % | weight % | Kind | D50 (μm) | weight % | retardancy 1.6 mm | afterflame time s/sample | Moldability |
| 14 | 69.5 | 0.5 | FA-A5 | 5.0 | 30 | V-0 | 0.3 | ○ |
| 15 | 69.5 | 0.5 | FA-A6 | 6.4 | 30 | V-0 | 0.6 | ○ |
| 16 | 69.5 | 0.5 | FA-A7 | 8.0 | 30 | V-0 | 2.3 | ○ |
| 17 | 69.5 | 0.5 | FA-A8 | 9.9 | 30 | V-0 | 5.0 | ○ |
| 18 | 69.5 | 0.5 | FA-A9 | 10.7 | 30 | Not V-2 | >30 | Δ |
| 19 | 69.5 | 0.5 | FA-A10 | 11.6 | 30 | Not V-2 | >30 | Δ |
| 20 | 69.5 | 0.5 | FA-A11 | 13.0 | 30 | Not V-2 | >30 | Δ |
| 21 | 69.5 | 0.5 | FA-A12 | 14.0 | 30 | Not V-2 | >30 | Δ |

As is clear from the results of Table 4 and FIG. 1, the resin compositions (Run Nos. 12 to 17) obtained by compounding a FA having a D50 of 1 to 10 μm into a polycarbonate type resin have superior flame retardancy and moldability. Therefore, it is considered that, when a FA having a D50 of 1 to 10 μm is compounded, the dispersibility of FA is good and the flame retardancy of the resulting resin composition is improved. The molded articles (Run Nos. 13 to 15) of resin compositions obtained by compounding a FA having a D50 of 3 to 7 μm into a polycarbonate type resin are strikingly improved in flame retardancy. Therefore, it is considered that, when a FA having a D50 of 3 to 7 μm is compounded into a polycarbonate type resin, the dispersibility of FA is better and the flame retardancy of the resulting resin composition is improved further.

Meanwhile, when a FA having a D50 outside a range of 1 to 10 μm is compounded (Run Nos. 10 to 11 and 18 to 21), the resulting flame retardancies are lower than the flame retardancy of used polycarbonate type resin per se, as is clear from Table 4 and FIG. 1.

Test Example 3

FA Use Amount Versus Flame Retardancy and Flexural Properties

PTFE and FA-A5 were compounded into PC in proportions shown in Table 5, to produce flame-retardant resin compositions. The compositions were evaluated for flame retardancy and average afterflame time by UL 94. The compositions were also examined for Flexural properties and moldability. The results are shown in Table 5. Relations between FA use amount and average afterflame time are shown in FIG. 2.

TABLE 5

| | Composition | | | Evaluation | | | | |
|---|---|---|---|---|---|---|---|---|
| Run No. | PC weight % | PTFE weight % | FA-A5 weight % | Flame retardancy 1.6 mm | Average afterflame time s/sample | Flexural strength MPa | Flexural modulus MPa | Moldability |
| 22 | 95.5 | 0.5 | 4 | Not V-2 | >30 | 102 | 2798 | ○ |
| 23 | 94.5 | 0.5 | 5 | V-0 | 6.7 | 103 | 2825 | ○ |
| 24 | 89.5 | 0.5 | 10 | V-0 | 1.2 | 103 | 3140 | ○ |
| 25 | 79.5 | 0.5 | 20 | V-0 | 1.0 | 101 | 3563 | ○ |
| 26 | 69.5 | 0.5 | 30 | V-0 | 0.6 | 97 | 4014 | ○ |
| 27 | 59.5 | 0.5 | 40 | V-0 | 0.8 | 75 | 5094 | ○ |
| 28 | 49.5 | 0.5 | 50 | V-0 | 4.8 | 75 | 5211 | ○ |
| 29 | 46.5 | 0.5 | 53 | Not V-2 | >30 | 50 | 5431 | Δ |

As is clear from the results of Table 5 and FIG. 2, the resin compositions (Run Nos. 23 to 28) obtained by compounding a FA having a given particle size, into a polycarbonate type resin in a proportion of 5 to 50 weight % are strikingly improved in flame retardancy. Therefore, it is considered that, when a FA is compounded into a polycarbonate type resin in a proportion of 5 to 50 weight %, the resulting resin composition is improved in flame retardancy because the ratio of resin component and FA in resin composition is appropriate.

Test Example 4

Evaluation of Flame Retardancies when Different Kinds of Inorganic Particles are Used There were produced flame-retardant resin compositions composed of 69.5 weight % of PC, 0.5 weight % of PTFE and 30 weight % of inorganic particles shown in Table 6. The compositions were evaluated for flame retardancy. The results are shown in Table 6.

TABLE 6

| | Composition | | | | | Evaluation | |
|---|---|---|---|---|---|---|---|
| Run No. | PC weight % | PTFE weight % | Inorganic particles Kind | D50 (μm) | weight % | Flame retardancy 1.6 mm | Average afterflame time s/sample |
| 30 | 69.5 | 0.5 | FA-A5 | 5.0 | 30 | V-0 | 0.6 |
| 31 | 69.5 | 0.5 | S | 3.0 | 30 | V-1 | 22.6 |
| 32 | 69.5 | 0.5 | HS | 3.0 | 30 | Not V-2 | >30 |

TABLE 6-continued

| | Composition | | | | | Evaluation | |
|---|---|---|---|---|---|---|---|
| | PC | PTFE | Inorganic particles | | | Flame retard- | Average afterflame |
| Run No. | weight % | weight % | Kind | D50 (μm) | weight % | ancy 1.6 mm | time s/sample |
| 33 | 69.5 | 0.5 | Al | 2.9 | 30 | V-1 | 19.7 |
| 34 | 69.5 | 0.5 | S | 3.0 | 15 | V-1 | 20.5 |
| | | | Al | 2.9 | 15 | | |

As is clear from Table 6, the case of using a FA (Run No. 30), as compared with the cases of using silicon dioxide (S or HS) or aluminum oxide (Al), is strikingly improved in flame retardancy. The reason therefor is that the FA is inorganic particles containing a complex containing silicon dioxide and aluminum oxide, which composite is not contained in particles (S or HS) composed only of silicon dioxide or in particles (Al) composed only of aluminum oxide.

Test Example 5

Comparison of Flame Retardancies when Different Resins are Used

PTFE (0.5 weight %) and FA-A5 were compounded in a thermoplastic resin shown in Table 7 in proportions shown in Table 7, to produce flame-retardant resin compositions. The compositions were evaluated for flame retardancy. The results are shown in Table 7.

TABLE 7

| | Composition | | | Evaluation | |
|---|---|---|---|---|---|
| Run No | Thermoplastic resin | | PTFE | FA-A5 | Flame retard-ancy | Average afterflame time |
| | Kind | weight % | weight % | weight % | 1.6 mm | s/sample |
| 35 | PC | 99.5 | 0.5 | 0 | Not V-2 | >30 |
| 36 | PC | 69.5 | 0.5 | 30 | V-0 | 0.6 |
| 37 | PET | 99.5 | 0.5 | 0 | Not V-2 | >30 |
| 38 | PET | 69.5 | 0.5 | 30 | Not V-2 | >30 |
| 39 | PBT | 99.5 | 0.5 | 0 | Not V-2 | >30 |
| 40 | PBT | 69.5 | 0.5 | 30 | Not V-2 | >30 |
| 41 | PP | 99.5 | 0.5 | 0 | Not V-2 | >30 |
| 42 | PP | 69.5 | 0.5 | 30 | Not V-2 | >30 |
| 43 | Ny | 99.5 | 0.5 | 0 | Not V-2 | >30 |
| 44 | Ny | 69.5 | 0.5 | 30 | Not V-2 | >30 |

As is clear from Table 7, no improvement in flame retardancy by use of FA is seen in the resin compositions using, as other thermoplastic resin, a polyethylene terephthalate (PET) (Run Nos. 37 and 38), a polybutylene terephthalate (PBT) (Run Nos. 39 and 40), a polypropylene (PP) (Run Nos. 41 and 42) or 6-nylon (Ny) (Run Nos. 43 and 44).

Therefore, it is understood that the improvement in flame retardancy is obtained by the unique synergism caused by combination use of a polycarbonate type resin and inorganic particles (including FA of particular particle sizes) containing particles containing a complex of silicon dioxide and aluminum oxide.

Thus, with a resin composition containing a polycarbonate resin and inorganic particles (including FA of particular particle sizes) containing particles containing a complex of silicon dioxide and aluminum oxide, there can be provided a flame-retardant, polycarbonate type resin composition high in flame retardancy and superior in melt fluidity and adaptability to environment, and a flame-retardant molding material or molded article containing the composition, at a low cost.

Thus, in the present invention, a flame-retardant resin composition which has higher flame retardancy with stressing a reduction in moldability can be provided. Particularly, when the inorganic particles used therein have a D50 of 3 to 7 μm, a flame-retardant resin composition is well balanced between flame-retardancy and moldability, mechanical properties, etc.

Test Example 6

Evaluation of Preventability for Elution of Heavy Metals, etc. by Use of Elution Preventer PC, PTFE, FA-A5 and an elution preventer (ferrous sulfate monohydrate or Schwertmanite) were used in amounts shown in Table 8 to produce flame-retardant resin compositions. The resin compositions were evaluated for flame retardancy. Also, when test pieces for evaluation of flame retardancy were produced, their appearances were observed visually to examine the generation and degree of silver (appearance). The results are shown in Table 8. Further, the resin compositions were quantitatively determined the amount of eluted metals subjected to a test for elution of heavy metals, etc. according to Environmental Agency Notification No. 46 (an elution test concerning Environmental Quality Standards for Soil Contamination). The results of the test for elution of heavy metals, etc. are shown in Table 9. For reference, the contents of heavy metals, etc. in FA-A5 are shown in Table 10.

Evaluation of Appearance

Appearance was evaluated based on the following standard.
○: Substantially no silver is observed.
Δ: Silver is observed slightly.
X: Silver is observed.

Test Method for Elution of Heavy Metals, etc. (According to an Elution Test Concerning Environmental Quality Standards for Soil Contamination (Environmental Agency Notification No. 46))

Sample: a given amount of pellets are taken and made into a kneaded material at 280° C. using a stone mortar-like extruder (a product of KCK, discharge rate: 8 kg/h). The kneaded material is freeze-ground and then passed through a non-metallic sieve (opening: 2 mm) to obtain a sample. Incidentally, pellets having diameters of 2 mm or less are used per se as a sample.

Preparation of solution for elution test: there are mixed a sample (unit: g) and a solvent (unit: ml) obtained by adding hydrochloric acid to pure water to allow the resulting solution to have a hydrogen ion index of 5.8 to 6.3, so that the total solution volume becomes 500 ml or more and the weight volume ratio becomes 10%.

Method for elution: the prepared solution for elution test is shaken for 6 hours continuously at normal temperature at normal pressure using a shaker whose shaking frequency has been adjusted to about 200 times per minute and whose shaking width has been adjusted to 4 to 5 cm.

Measurement of elution amounts: a sample solution obtained by the above operation is allowed to stand for 10 to 30 minutes and then centrifuged at abut 3,000 rpm for 20 minutes; the supernatant liquid is filtered through a membrane filter having a pore size of 0.45 μm to collect a filtrate; the amounts of chromium(VI), arsenic, selenium, lead and mercury contained in the filtrate are measured by ICP emission spectral analysis or atomic absorption spectroscopy, to take them as eluted amounts.

TABLE 8

| Run No. | PC weight % | PTFE weight % | FA-A5 weight % | Elution preventer Kind | Elution preventer weight % | Elution preventer Ratio to FA | Flame retardancy 1.6 mm | Average afterflame time s/sample | Appearance |
|---|---|---|---|---|---|---|---|---|---|
| 45 | 69.5 | 0.5 | 30.0 | — | 0 | 0 | V-0 | 0.6 | ○ |
| 46 | 69.47 | 0.5 | 30.0 | FD-1 | 0.03 | 1/1000 | V-0 | 0.5 | ○ |
| 47 | 69.45 | 0.5 | 30.0 | FD-1 | 0.05 | 1/600 | V-0 | 0.5 | ○ |
| 48 | 69.2 | 0.5 | 30.0 | FD-1 | 0.3 | 1/100 | V-0 | 0.5 | ○ |
| 49 | 68.5 | 0.5 | 30.0 | FD-1 | 1 | 1/30 | V-0 | 0.5 | ○ |
| 50 | 68.0 | 0.5 | 30.0 | FD-1 | 1.5 | 1/20 | V-0 | 0.5 | Δ |
| 51 | 67.5 | 0.5 | 30.0 | FD-1 | 2 | 1/15 | V-0 | 1.5 | X |
| 52 | 69.47 | 0.5 | 30.0 | SW | 0.03 | 1/1000 | V-0 | 0.5 | ○ |
| 53 | 69.45 | 0.5 | 30.0 | SW | 0.05 | 1/600 | V-0 | 0.5 | ○ |
| 54 | 69.2 | 0.5 | 30.0 | SW | 0.3 | 1/100 | V-0 | 0.5 | ○ |
| 55 | 68.5 | 0.5 | 30.0 | SW | 1 | 1/30 | V-0 | 0.5 | ○ |
| 56 | 68.0 | 0.5 | 30.0 | SW | 1.5 | 1/20 | V-0 | 0.5 | Δ |
| 57 | 67.5 | 0.5 | 30.0 | SW | 2 | 1/15 | V-0 | 1.5 | X |

TABLE 9

| Run No. | Elution preventer Kind | Elution preventer Ratio to FA | Cr (VI) | As | Se | Pb | Hg |
|---|---|---|---|---|---|---|---|
| 45 | — | 0 | 0.01 | 0.004 | 0.003 | <0.005 | <0.0005 |
| 46 | FD-1 | 1/1000 | <0.01 | <0.001 | <0.001 | <0.005 | <0.0005 |
| 47 | FD-1 | 1/600 | <0.01 | <0.001 | <0.001 | <0.005 | <0.0005 |
| 48 | FD-1 | 1/100 | <0.01 | <0.001 | <0.001 | <0.005 | <0.0005 |
| 49 | FD-1 | 1/30 | <0.01 | <0.001 | <0.001 | <0.005 | <0.0005 |
| 50 | FD-1 | 1/20 | <0.01 | <0.001 | <0.001 | <0.005 | <0.0005 |
| 51 | FD-1 | 1/15 | <0.01 | <0.001 | <0.001 | <0.005 | <0.0005 |
| 52 | SW | 1/1000 | <0.01 | <0.001 | <0.001 | <0.005 | <0.0005 |
| 53 | SW | 1/600 | <0.01 | <0.001 | <0.001 | <0.005 | <0.0005 |
| 54 | SW | 1/100 | <0.01 | <0.001 | <0.001 | <0.005 | <0.0005 |
| 55 | SW | 1/30 | <0.01 | <0.001 | <0.001 | <0.005 | <0.0005 |
| 56 | SW | 1/20 | <0.01 | <0.001 | <0.001 | <0.005 | <0.0005 |
| 57 | SW | 1/15 | <0.01 | <0.001 | <0.001 | <0.005 | <0.0005 |
| 45 | — | 0 | 0.01 | 0.004 | 0.003 | <0.005 | <0.0005 |

Test for dissolving-out of heavy metals, etc. (mg/liter)

TABLE 10

| Analysis item | Content in FA-A5 ppm |
|---|---|
| Total chromium compounds | 2.4 (as Cr metal) |
| Arsenic and its compounds | 12 (as As element) |
| Selenium and its compounds | 11 (as Se element) |
| Lead and its compounds | 73 (as Pb metal) |
| Total mercury | 0.28 (as Hg Metal) |

As is clear from Table 9, in the case of a resin composition (Run No. 45) containing a polycarbonate type resin and inorganic particles containing a FA of particular particle sizes, there is, in the elution test, elution of very small amounts of chromium(VI), arsenic and selenium which are heavy metals, etc. However, by compounding, as an elution preventer, ferrous sulfate monohydrate or Schwertmanite into the resin composition in an amount of 1/1,000 or more (relative to FA), the elution of heavy metals, etc. can be suppressed while high flame retardancy is kept. Also, as seen in Table 8, when an elution preventer is compounded into the resin composition in an amount of less than 2.0 weight %, preferably in an amount of less than 1.5 weight %, there is no generation of silver during molding and therefore the resulting molded article has enhanced appearance.

In the above, the present invention has been described by way of Examples. These Examples are only exemplary and it is easily understood by any person skilled in the art that various modifications are possible and such modifications also are included in the range of the present invention.

In these Examples, there were used FA as the inorganic particles containing a complex of silicon dioxide and aluminum oxide. However, there can also be used an ash obtained by burning wood or the like, silica-alumina complex particles, etc. as long as they have a composition, particle sizes, etc. specified by the present invention.

INDUSTRIAL APPLICABILITY

The flame-retardant resin composition of the present invention has superior flame retardancy and accordingly is useful for applications requiring flame retardancy, especially packages of electric or electronic appliances.

The invention claimed is:

1. A flame-retardant resin composition comprising a polycarbonate type resin and fly ash which contains particles composed of a complex of silicon dioxide and aluminum oxide and has a 50% particle size (D50) of 1 to 10 μm and has two peaks in its particle size distribution, wherein the peak corresponding to the particle size distribution of larger particles is greater than the peak corresponding to the particle size distribution of smaller particles, the ratio of the average particle size of the peak corresponding to the particle size distribution of larger particles to the average particle size of the peak corresponding to the particle size distribution of smaller particles is less than or equal to 10.0, and the amount of the fly ash containing particles having particle size of 20 μm or less is 70 weight % or more, wherein the fly ash is contained in the total composition in an amount of 1 to 60 weight %, and wherein the flame-retardant resin composition has a flame retardancy of V-0 in the UL94V method.

2. A flame-retardant resin composition according to claim 1, which contains an elution preventer for preventing the elution of components present in the fly ash.

3. A flame-retardant resin composition according to claim 1, wherein the fly ash contains:
   (a) 44 to 80 weight % of silicon dioxide,
   (b) 15 to 40 weight % of aluminum oxide; and
   (c) $Fe_2O_3$, $TiO_2$, MgO and CaO as further components.

4. A flame-retardant resin composition according to claim 1, which further contains a fiber-formable fluorinated polymer in an amount of 0.05 to 5 weight % based on the total flame-retardant resin composition.

5. A flame-retardant molding material containing a flame-retardant resin composition according to claim 1.

6. A molded article obtained by molding a flame-retardant resin composition according to claim 1.

7. A flame-retardant resin composition according to claim 2, wherein the elution preventer is an adsorbent capable of adsorbing components present in the fly ash, or an ion exchange resin.

8. A flame-retardant resin composition according to claim 2, wherein the elution preventer for preventing the dissolving-out of components present in the fly ash is selected from ferrous sulfate mono-hydrate and Schwertmannite.

9. A flame-retardant resin composition according to claim 3, wherein the total amount of the total silicon dioxide and the total aluminum oxide in the fly ash is 60 weight % or more in the total fly ash.

10. A flame-retardant molding material according to claim 5, wherein the flame-retardant resin composition is compounded into a thermoplastic resin other than a polycarbonate resin.

* * * * *